United States Patent
Song et al.

(10) Patent No.: US 10,405,995 B2
(45) Date of Patent: Sep. 10, 2019

(54) ARTIFICIAL LIMB STRUCTURE HAVING MAGNETIC LOCK DEVICE

(71) Applicant: KOREA WORKERS' COMPENSATION & WELFARE SERVICE, Seoul (KR)

(72) Inventors: Jeom Sik Song, Incheon (KR); Suk Min Lee, Incheon (KR); Sin Gi Kim, Seoul (KR); Do Wan Kim, Uijeongbu-si (KR); Jei Cheong Ryu, Seoul (KR)

(73) Assignee: KOREA WORKS' COMPENSATION & WELFARE SERVICE, Seoul (KR)

( * ) Notice: Subject to any disclaimer, the term of this patent is extended or adjusted under 35 U.S.C. 154(b) by 0 days.

(21) Appl. No.: 15/557,530

(22) PCT Filed: Mar. 12, 2015

(86) PCT No.: PCT/KR2015/002425
§ 371 (c)(1),
(2) Date: Sep. 12, 2017

(87) PCT Pub. No.: WO2016/143928
PCT Pub. Date: Sep. 15, 2016

(65) Prior Publication Data
US 2018/0055657 A1    Mar. 1, 2018

(30) Foreign Application Priority Data
Mar. 12, 2015    (KR) .................. 10-2015-0034688

(51) Int. Cl.
*A61F 2/78*    (2006.01)
*A61F 2/54*    (2006.01)
(Continued)

(52) U.S. Cl.
CPC .................. *A61F 2/60* (2013.01); *A61F 2/54* (2013.01); *A61F 2/78* (2013.01); *A61F 2/7812* (2013.01);
(Continued)

(58) Field of Classification Search
CPC .. A61F 2/54; A61F 2/60; A61F 2/7812; A61F 2/80; A61F 2002/30079; A61F 2002/6863; A61F 2210/009; A43B 1/0054
See application file for complete search history.

(56) References Cited

U.S. PATENT DOCUMENTS 4,055,824 A * 10/1977 Baermann .............. B23Q 3/152
                                                    335/288
4,314,219 A * 2/1982 Haraguchi ................ H01F 7/04
                                                    294/65.5
(Continued)

FOREIGN PATENT DOCUMENTS

EP    0808013    11/1997
KR    101102615 A    6/2011
(Continued)

OTHER PUBLICATIONS

International Search Report of PCT/KR2015/002425, dated Sep. 1, 2015, English Translation.

*Primary Examiner* — Christie L Bahena
(74) *Attorney, Agent, or Firm* — STIP Law Group, LLC

(57) ABSTRACT

Provided is an artificial limb structure having a magnetic lock device. The artificial limb structure includes: an artificial limb coupled to a magnetic lock device; and a socket liner unit detachably coupled to the magnetic lock device, wherein the socket liner unit includes an attachment and detachment member attachable and detachable to/from the magnetic lock device by a magnetic force, and the magnetic lock device includes: permanent magnets; a magnetic flux control unit provided on the permanent magnets and trans- (Continued)

mitting the magnetic force generated by the permanent magnets to the attachment and detachment member or interrupting a transmission of the magnetic force; a magnetic force interrupting unit provided at the magnetic flux control unit and interrupting magnetic forces between permanent magnets arranged at opposite sides of the magnetic force interrupting unit; and a switch unit adjusting an arrangement of the permanent magnets with respect to the magnetic force interrupting unit.

13 Claims, 11 Drawing Sheets

(51) Int. Cl.
  *A61F 2/80* (2006.01)
  *A61F 2/60* (2006.01)
  *A61F 2/68* (2006.01)
(52) U.S. Cl.
  CPC ........ *A61F 2/80* (2013.01); *A61F 2002/6854* (2013.01); *A61F 2002/7868* (2013.01); *A61F 2210/009* (2013.01)

(56) References Cited

U.S. PATENT DOCUMENTS

| 5,507,835 | A | * | 4/1996 | Jore | A61F 2/38 |
| | | | | | 623/33 |
| 6,273,918 | B1 | | 8/2001 | Yuhasz | |
| 6,707,360 | B2 | * | 3/2004 | Underwood | B23Q 3/1546 |
| | | | | | 269/8 |
| 7,817,004 | B2 | | 10/2010 | Fullerton et al. | |
| 7,922,773 | B1 | * | 4/2011 | Kuiken | A61F 2/54 |
| | | | | | 623/24 |
| 8,057,550 | B2 | | 11/2011 | Clausen et al. | |
| 8,206,459 | B1 | * | 6/2012 | Lock | A61F 2/78 |
| | | | | | 24/303 |
| 8,217,743 | B2 | * | 7/2012 | Liu | B23D 47/025 |
| | | | | | 335/285 |
| 8,698,363 | B2 | | 4/2014 | Utsumi et al. | |
| 2006/0111792 | A1 | * | 5/2006 | Shannon | A61F 2/7812 |
| | | | | | 623/36 |
| 2009/0288316 | A1 | * | 11/2009 | Fullerton | A43B 1/0054 |
| | | | | | 36/116 |
| 2009/0292371 | A1 | * | 11/2009 | Fullerton | A61C 8/0081 |
| | | | | | 623/57 |
| 2010/0251574 | A1 | * | 10/2010 | Battlogg | A43B 5/0405 |
| | | | | | 36/117.1 |
| 2012/0143350 | A1 | * | 6/2012 | Song | A61F 2/76 |
| | | | | | 623/33 |
| 2013/0289743 | A1 | * | 10/2013 | Abu Osman | A61F 2/7812 |
| | | | | | 623/36 |
| 2015/0013191 | A1 | * | 1/2015 | Brown | A43B 21/00 |
| | | | | | 36/102 |

FOREIGN PATENT DOCUMENTS

| KR | 1020120106746 | 9/2012 |
| WO | WO2011057177 A1 | 5/2011 |
| WO | WO2011065608 A1 | 6/2011 |
| WO | WO2015144073 A1 | 10/2015 |

* cited by examiner

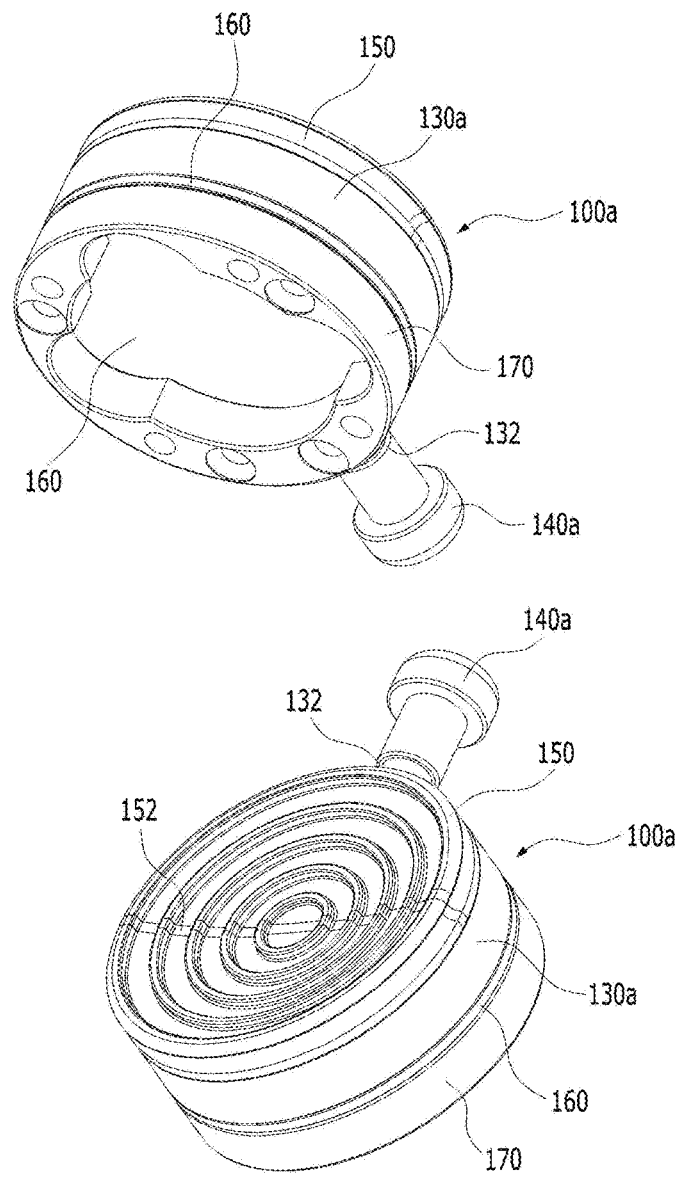
[FIG. 2]

[FIG. 3]
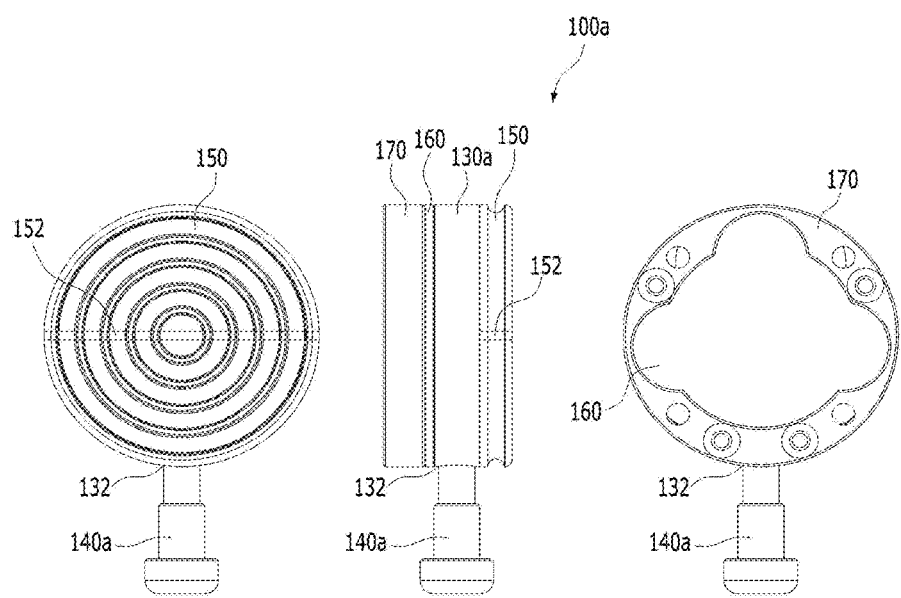

[FIG. 4]
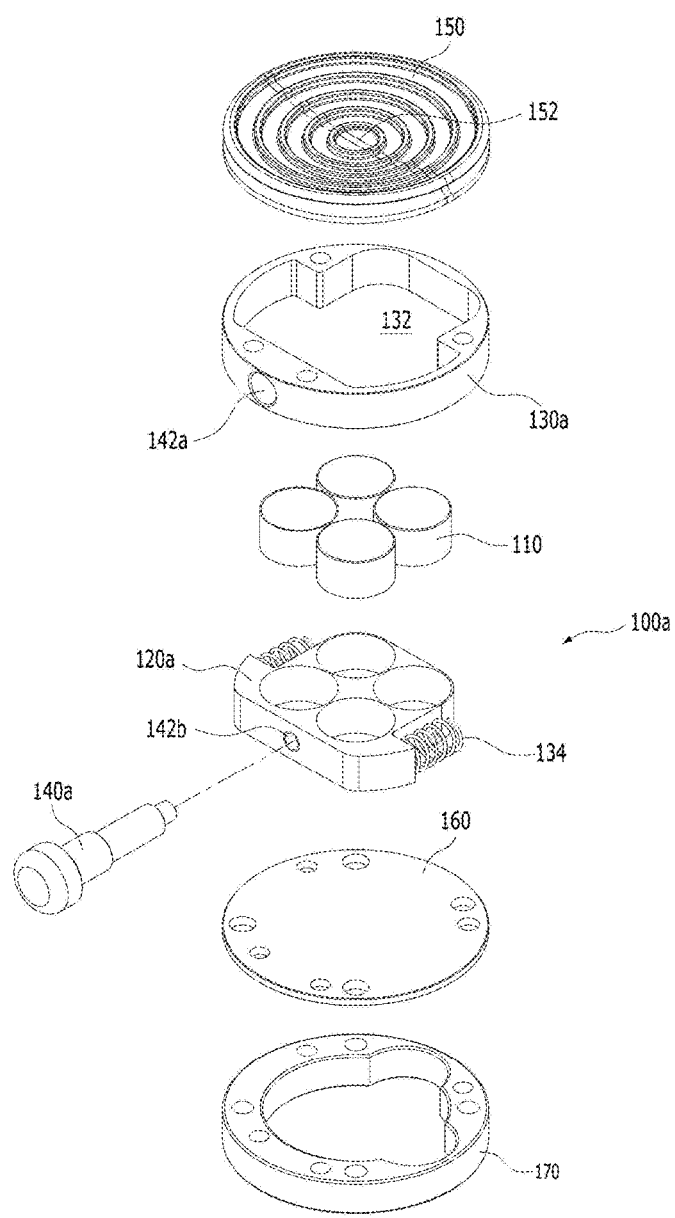

[FIG. 5]
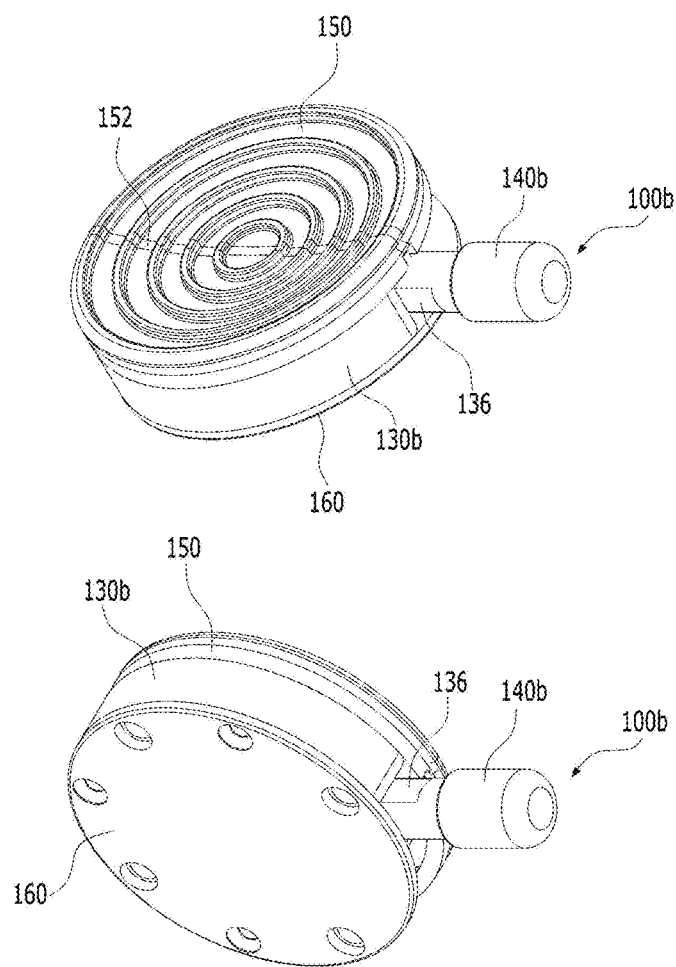

[FIG. 6]
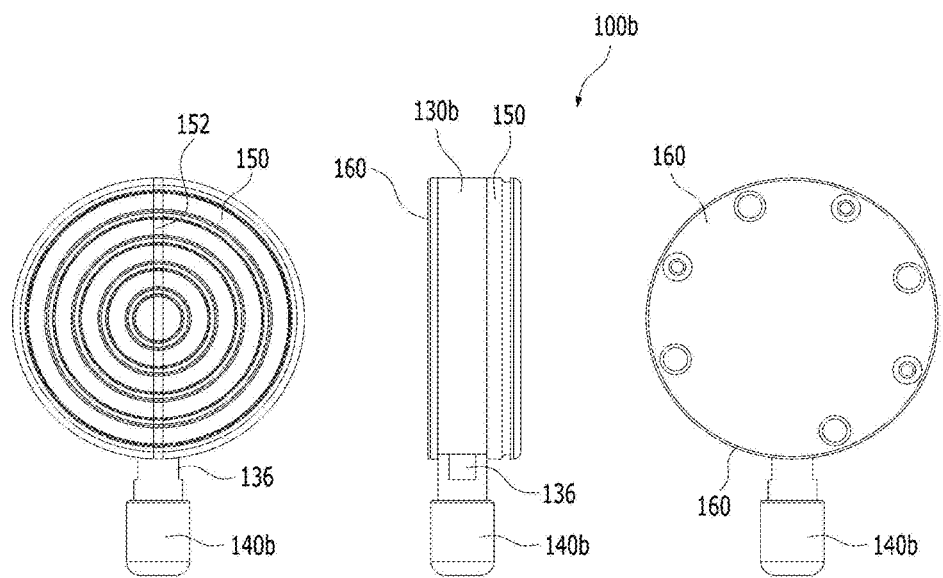

[FIG. 7]
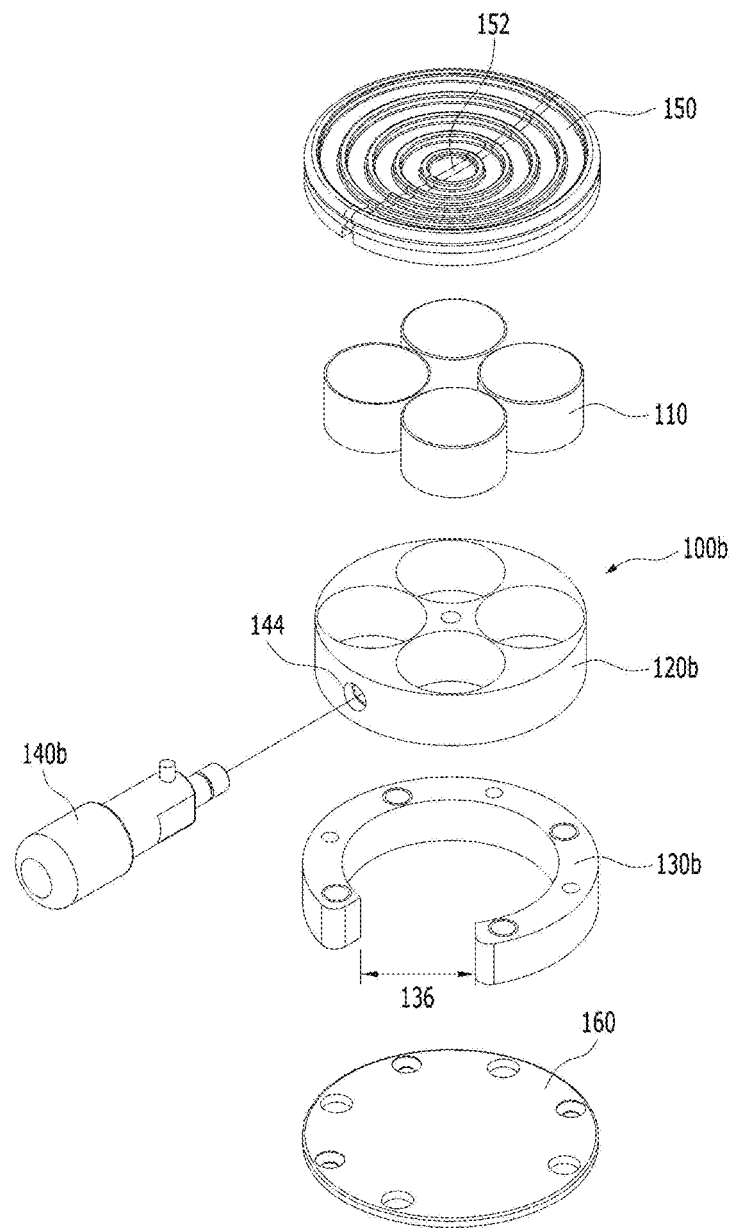

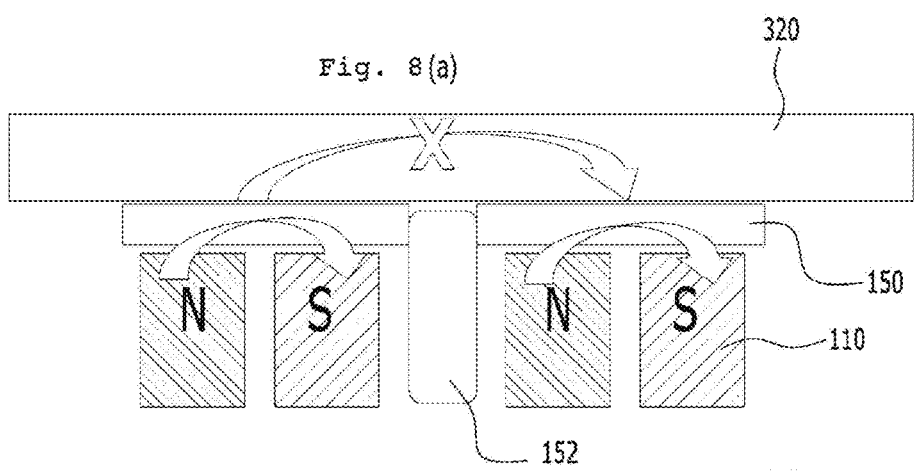
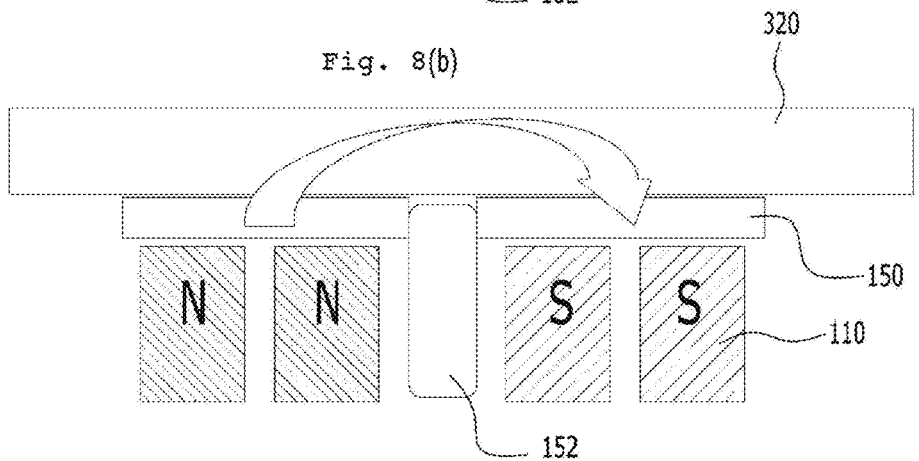

[FIG. 11]
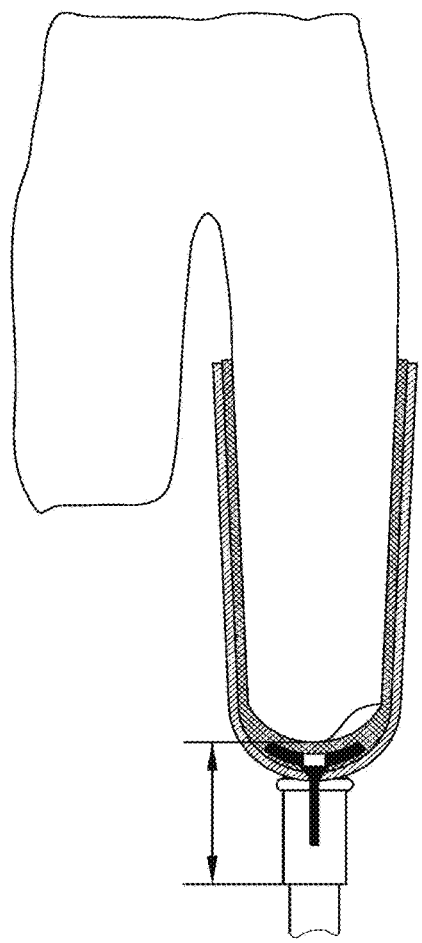

ARTIFICIAL LIMB STRUCTURE HAVING MAGNETIC LOCK DEVICE

CROSS-REFERENCE TO RELATED APPLICATIONS

This application is the U.S. National Phase under 35 U.S.C. § 371 of International Application No. PCT/KR2015/002425 filed on Mar. 12, 2015, which in turn claims the benefit of Korean Application No. 10-2015-0034688, filed on Mar. 12, 2015, the disclosures of which are incorporated by reference into the present application.

TECHNICAL FIELD

The present invention relates generally to an artificial limb structure. More particularly, the present invention relates to an artificial limb structure, in which the artificial limb structure is provided with a magnetic lock device using a permanent magnet such that a stump of a wearer and an artificial limb are connected to each other, whereby attachment and detachment of the artificial limb is facilitated, and a secure and comfortable fit of the artificial limb is enhanced.

BACKGROUND ART

As well known in the art, artificial limbs are man-made devices that are fabricated such that their appearance or function can replace that of a missing part of an arm or a leg. Some types of artificial limbs have the same shape and function as those of a missing joint. Although there are several categories of artificial limbs depending on the purpose and parts to be used, they are generally divided into an upper artificial limb that is commonly referred to as an artificial arm and a lower artificial limb that is commonly referred to as an artificial leg.

In order to use an artificial limb, first, a socket liner is worn on a stump of a wearer, and the artificial limb is then connected to the socket liner. Most devices for connecting the artificial limb to the socket liner in the related art use a pin lock, which fixes the artificial limb and the socket liner using a pin. The pin lock is a type of locking mechanism in which the socket liner is connected to the artificial limb by fixing a metal pin to the distal connecting end of the socket liner. In the case of the pin lock, the area where the stump of the wearer and the artificial limb are connected to each other is only the cross-sectional area of the pin. Consequently, it is difficult to balance the weight of the body in the standing position, and a gap in a fastening portion causes noises when walking.

FIG. 11 is a view showing a fastening structure of an artificial limb structure having a conventional pin lock device. As shown in the figure, the pin lock has a long connecting portion where the stump of the wearer and the artificial limb are connected to each other. This structure, however, is difficult to use if the stump of the wearer is long. In addition, since the area where the artificial limb and the socket liner are connected is small, high pressure is applied to the stump of the wearer when walking, which may cause abrasion and the like, and it is difficult to precisely align and attach the artificial limb to the hole of the pin lock.

In the case of Korean Patent No. 10-1102615 filed and patented by the applicant of the present invention, a magnetic lock device including an electro-permanent magnet composed of a permanent magnet and an electromagnet is used in an artificial limb structure, so the artificial limb and the socket liner can be easily attached to and detached from each other. However, the magnetic lock device still has the inconvenience of requiring power to be supplied thereto.

DISCLOSURE

Technical Problem

Accordingly, the present invention has been made keeping in mind the above problems occurring in the prior art, and an object of the present invention is to provide an artificial limb structure, in which the artificial limb structure is provided with a magnetic lock device capable of being attachable and detachable without electric power supplied thereto, whereby the attachment and detachment of the artificial limb to/from the socket liner is facilitated, and the socket liner and the artificial limb connection area is increased, thereby enhancing the comfortable fit.

Technical Solution

In order to accomplish the above object, the present invention provides a an artificial limb structure having a magnetic lock device, the artificial limb structure including: an artificial limb coupled at an upper end thereof to a magnetic lock device; and a socket liner unit detachably coupled to the magnetic lock device coupled to the artificial limb, wherein the socket liner unit includes an attachment and detachment member attachable and detachable to/from the magnetic lock device by a magnetic force, and the magnetic lock device includes: permanent magnets; a magnetic flux control unit provided on the permanent magnets and transmitting the magnetic force generated by the permanent magnets to the attachment and detachment member or interrupting a transmission of the magnetic force; a magnetic force interrupting unit provided at the magnetic flux control unit and interrupting magnetic forces between permanent magnets arranged at opposite sides of the magnetic force interrupting unit; and a switch unit adjusting an arrangement of the permanent magnets with respect to the magnetic force interrupting unit.

The switch unit may be adjusted such that the permanent magnets of the same polarity are placed at the opposite sides of the magnetic force interrupting unit, respectively, so that the magnetic lock device and the attachment and detachment member are attached to each other, or the permanent magnets of opposite polarities are placed at least at one of the opposite sides of the magnetic force interrupting unit so that the magnetic lock device and the attachment and detachment member are detached from each other.

The switch unit may allow the permanent magnets to be moved linearly horizontally so that a relative arrangement of polarities of the permanent magnets to the magnetic force interrupting unit is changed.

The switch unit may allow the permanent magnets to be rotated and moved horizontally so that a relative arrangement of polarities of the permanent magnets to the magnetic force interrupting unit is changed.

The magnetic lock device may further include: a magnet mounting unit in which the permanent magnets are installed; and a magnetic casing provided with a magnet receiving hole receiving therein the magnet mounting unit, the magnetic flux control unit may be provided on the magnetic casing and may transmit the magnetic force generated by the permanent magnets to the attachment and detachment member or interrupt the transmission of the magnetic force, the magnetic force interrupting unit may be linearly provided at a center of the magnetic flux control unit and may interrupt the magnetic forces between the permanent magnets arranged at the opposite sides of the magnetic force interrupting unit, and the switch unit may be connected to the magnet mounting unit and may adjust the arrangement of the permanent magnets with respect to the magnetic force interrupting unit.

The switch unit may be connected to the magnet mounting unit, and may be installed to pass through a side surface of the magnetic casing, the switch unit allowing the permanent magnets to be moved linearly in a direction perpendicular to the linear magnetic force interrupting unit so that a relative arrangement of polarities of the permanent magnets to the magnetic force interrupting unit may be changed.

The magnetic casing may be provided with an opening partially formed at a side surface of the magnetic casing, and the switch unit may be connected to the magnet mounting unit and may be installed to pass through the opening of the magnetic casing, the switch unit allowing the permanent magnets to be rotated and moved linearly with respect to the linear magnetic force interrupting unit so that a relative arrangement of polarities of the permanent magnets to the linear magnetic force interrupting unit may be changed.

The artificial limb structure having the magnetic lock device may further include a magnetic force amplifying unit provided at a lower portion of the magnetic casing and amplifying the magnetic force generated by the permanent magnets.

The artificial limb structure having the magnetic lock device may further include a socket receiving therein the socket liner unit and connected to an outer circumferential surface of the magnetic lock device.

The artificial limb structure having the magnetic lock device may further include an elastic member connecting the magnet mounting unit and the magnetic casing to each other, and restoring the magnet mounting unit to its original position when an external force to move the magnet mounting unit is removed.

The socket liner unit may include: a socket liner umbrella; a socket liner provided at an upper end of the socket liner umbrella and applied to a stump of a wearer; and the attachment and detachment member attached to a lower portion of the socket liner umbrella, and attachable and detachable to/from the magnetic lock device by the magnetic force, the attachment and detachment member being made of a metal material.

The socket liner may include a silicone material.

An inner surface of the socket liner that is in contact with the stump of the wearer may be made of a silicone material having a Shore A hardness ranging from 3 to 20.

An outer surface of the socket liner that is in contact with the socket liner umbrella is attached with a span fabric, or the outer surface of the socket liner may be covered with a parylene coating.

Advantageous Effects

According to the artificial limb structure of the present invention, by providing the magnetic lock device capable of being attachable and detachable without electric power supplied thereto, the attachment and detachment of the artificial limb to/from the socket liner can be facilitated, and the socket liner and the artificial limb connection area can be increased, thereby enhancing the comfortable fit.

DESCRIPTION OF DRAWINGS

FIG. 2 is a perspective view showing a first magnetic lock device 100a.

FIG. 3 is a top, side, and bottom view showing the first magnetic lock device 100a of the present invention.

FIG. 4 is an exploded perspective view showing the first magnetic lock device 100a.

FIG. 5 is a perspective view showing a second magnetic lock device 100b.

FIG. 6 is a top, side, and bottom view showing the second magnetic lock device 100b of the present invention.

FIG. 7 is an exploded perspective view showing the second magnetic lock device 100b.

FIGS. 8a and 8b are conceptual views showing a basic principle of attachment and detachment of the artificial limb structure having the magnetic lock device of the present invention.

FIGS. 9a and 9b are conceptual views showing a principle of attachment and detachment of the artificial limb structure having the first magnetic lock device 100a.

FIG. 11 is a view showing a fastening structure of an artificial limb structure having a conventional pin lock device.

BEST MODE

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims. In the following description of the present invention, detailed descriptions of known functions and components incorporated herein will be omitted when it may make the subject matter of the present invention unclear.

It will be understood that, although the terms first, second, etc. may be used herein to describe various elements, these elements should not be limited by these terms. These terms are only used to distinguish one element, from another element.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Figures 1A, 1B:
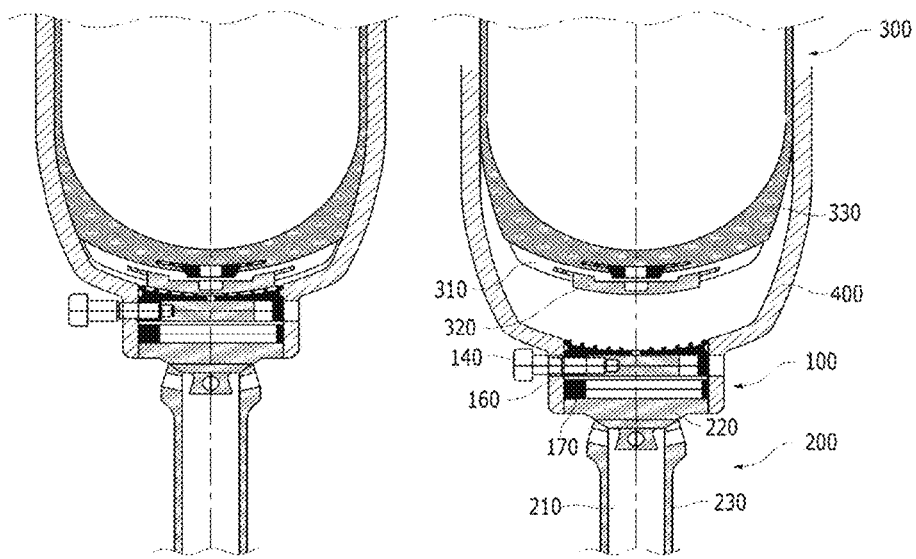
FIGS. 1a and 1b are side cross-sectional views showing a structure of an artificial limb structure having a magnetic lock device according to an embodiment of the present invention.

Hereinbelow, exemplary embodiments of the present invention will be described in detail with reference to the accompanying drawings. Wherever possible, the same reference numerals will be used throughout the drawings and the description to refer to the same or like elements or parts, and redundant descriptions thereof are omitted FIGS. 1a and 1b are side cross-sectional views showing a structure of an artificial limb structure having a magnetic lock device according to an embodiment of the present invention. Here, FIG. 1a shows a state in which an artificial limb 200 and a socket liner unit 300 are attached to each other, and FIG. 1b shows a state in which the artificial limb 200 and the socket liner unit 300 are detached from each other.

Hereinafter, the structure of the artificial limb structure having the magnetic lock device according to the embodiment of the present invention will be described with reference to FIGS. 1a and 1b.

The artificial limb structure having the magnetic lock device of the present invention includes the artificial limb 200 coupled at an upper end thereof to a magnetic lock device 100, and the socket liner unit 300 detachably coupled to the magnetic lock device 100 coupled to the artificial limb 200.

The socket liner unit 300 includes an attachment and detachment member 320 attachable and detachable to/from the magnetic lock device 100 by a magnetic force.

The magnetic lock device 100 includes permanent magnets, a magnet casing 130, a magnetic flux control unit 150, a magnetic force interrupting unit, and a switch unit 140, and may be attached or detached to/from the attachment and detachment member 320 by controlling the flow of magnetic flux. The structure and operation principle of the magnetic lock device 100 will be described in detail below with reference to two examples of a first magnetic lock device 100a and a second magnetic lock device 100b.

The artificial limb 200 includes an artificial limb body 210, an artificial limb connecting pyramid 220, and an artificial limb connecting adaptor 230.

The artificial limb connecting pyramid 220 is installed at an upper portion of the artificial limb body 210, and is coupled to the magnetic lock device 100 to connect the artificial limb body 210 and the magnetic lock device 100 to each other. The artificial limb connecting pyramid 220 may be made of aluminum, titanium, stainless steel or the like, but the scope of the present invention is not limited thereto.

The artificial limb connecting adaptor 230 surrounds the artificial limb body 210, and is installed at a lower portion of the artificial limb connecting pyramid 220, the artificial limb connecting adaptor being installed to surround an outer periphery of the artificial limb body 210 such that the artificial limb connecting pyramid 220 is coupled to the artificial limb body.

The socket liner unit 300 includes a socket liner umbrella 310, the attachment and detachment member 320, and a socket liner 330.

The socket liner umbrella 310 is provided at a lower portion of the socket liner 330, and receives therein the socket liner 330, the socket liner umbrella being coupled at a lower end thereof to the attachment and detachment member 320 connected to the socket liner 330.

The socket liner 330 is a cushioning material installed at an upper end of the socket liner umbrella 310, and may be directly applied to the stump of a wearer. The socket liner 330 may be made of a silicone material that is comfortable to the human body, but the scope of the present invention is not limited thereto.

The socket liner 330 may have a dual structure. Specifically, an inner surface of the socket liner that is in contact with the stump of the wearer may be made by shaping a low-hardness silicone material (Shore [0029] A hardness ranging from 3 to 20) in order to afford a smooth and comfortable sensation when worn. In addition, an outer surface of the socket liner that is in contact with the socket liner umbrella 310 of the socket liner 330 may be attached with a span fabric (not shown), or may be covered with a parylene coating, the socket liner umbrella of the socket liner being not in direct contact with the stump of the wearer.

Parylene coating is a coating method in which a dimer in powder form is deposited by chemical vapor deposition (CVD) to form a polymer film. Specifically, the dimer in powder form is converted into a gaseous dimer by pyrolysis, and gas particles are polymerized under a vacuum state and coated in film form on the surface of the object to be treated. Due to such characteristics, a uniform coating film can be formed regardless of the surface shape of the object, and thus it can serve as an excellent protective film.

Specifically, the span fabric may be a unidirectional span fabric in the case of a socket liner for the lower leg, and may be a bidirectional span fabric in the case of a socket liner for the thigh. When the wearer walks for a long time wearing the artificial limb, the socket liner 330 repeatedly expands and contracts due to the weight of the artificial limb. As a result, the surface of the socket liner 330 and the wearer's skin continuously rub against each other, which may cause abrasion on the skin. Such a problem can be solved by using the span fabric.

The socket 400 is installed to surround an outer circumferential surface of the magnetic lock device 100, and serves to receive therein and stably support the socket liner unit 300 coupled to the magnetic lock device 100.

FIG. 2 is a perspective view showing the first magnetic lock device 100a, FIG. 3 is a top, side, and bottom view showing the first magnetic lock device 100a of the present invention, and FIG. 4 is an exploded perspective view showing the first magnetic lock device 100a.

Hereinafter, the first magnetic lock device 100a included in the artificial limb structure having the magnetic lock device according to the embodiment of the present invention will be described with reference to FIGS. 2 to 4.

Referring to FIG. 2, the first magnetic lock device 100a included in the artificial limb structure having the magnetic lock device according to the embodiment of the present invention includes: the permanent magnets 110; a magnet mounting unit 120a; a magnetic casing 130a; an elastic member; a switch unit 140a; the magnetic flux control unit 150, a magnetic force amplifying unit 160, and a pyramid fixing unit 170.

As shown in the drawings, the permanent magnets 110 may be composed of two pairs of permanent magnets having opposite polarities to each other.

The magnet mounting unit 120a is a structure in which the permanent magnets are installed in a predetermined arrangement.

The magnetic casing 130a is provided at a center thereof with a magnet receiving hole 132, and the magnet mounting unit 120a is received in the magnet receiving hole 132.

The magnetic flux control unit 150 is provided on the magnetic casing 130a, and controls the flow of magnetic flux such that the magnetic force generated by the permanent magnets 110 is transmitted or interrupted to/from the attachment and detachment member 320.

The magnetic force interrupting unit 152 is linearly formed at a center of the magnetic flux control unit 150, and magnetic forces between the permanent magnets 110 may be interrupted with respect to the linear magnetic force interrupting unit 152.

The switch unit 140a is connected to a side surface of the magnet mounting unit 120a, and is installed to pass through a side surface of the magnetic casing, such that a position of the magnet mounting unit 120a is horizontally moved.

The switch unit 140a is installed to pass through the side surface of the magnetic casing 130a, and is operated to move the permanent magnets 100 in a direction perpendicular to the linear magnetic force interrupting unit 152.

Specifically, the switch unit 140a is connected to the magnet mounting unit 120a through a switch unit coupling hole b 142b, and is installed to pass through the side surface of the magnetic casing 130a through a switch unit coupling hole a 142a, whereby the permanent magnets 110 can be horizontally moved in the direction perpendicular to the linear magnetic force interrupting unit 152. Thus, the arrangement of polarities of the permanent magnets 110 can be determined relative to the magnetic force interrupting unit 152.

For example, the permanent magnets may be arranged such that opposite polarities, that is, N poles and S poles, are arranged at opposite sides of the magnetic force interrupting unit 152, respectively, so that polarities of the permanent magnets may be separated. Alternatively, the permanent magnets may be arranged such that N poles and S poles coexist at least at one of the opposite sides of the magnetic force interrupting unit 152.

The elastic member 134 connects the magnet mounting unit 120a and the magnetic casing 130a to each other, and serves to restore the magnet mounting unit 120a to its original position when the magnet mounting unit 120a is moved horizontally by an external force applied through the switch unit 140a and then the external force is removed.

The magnetic force amplifying unit 160 is installed at a lower portion of the magnetic casing 130a, and serves to amplify the magnetic force generated by the permanent magnets 110.

The pyramid fixing unit 170 is coupled to the artificial limb connecting pyramid of the artificial limb (200 in FIG. 1) to connect the magnetic lock device 100a and the artificial limb 200 to each other.

FIG. 5 is a perspective view showing the second magnetic lock device 100b, FIG. 6 is a top, side, and bottom view showing the second magnetic lock device 100b of the present invention, and FIG. 7 is an exploded perspective view showing the second magnetic lock device 100b.

Hereinafter, the second magnetic lock device 100b included in the artificial limb structure having the magnetic lock device according to the embodiment of the present invention will be described with reference to FIGS. 5 to 7.

Referring to FIGS. 5 to 7, the configurations constituting the second magnetic lock device 100b are the same as those of the first magnetic lock device 100a described above, so a detailed description thereof will be omitted.

However, the structure and operation of a magnet mounting unit 120b, a magnetic casing 130b, and a switch unit 140b of the second magnetic lock device 100b are different from the magnet mounting unit 120a, the magnetic casing 130a, and the switch unit 140a of the first magnetic lock device 100a. Accordingly, the horizontal movement of the permanent magnets may be implemented in a rotary motion rather than a linear motion.

Specifically, the magnet mounting unit 120b is a structure in which the permanent magnets 110 are installed, and may be formed in a cylinder shape.

The magnetic casing 130b is provided at a center thereof with a magnet receiving hole 132b receiving therein the magnet mounting unit 120b, and may have a ring shape having an opening 136 partially formed at a side surface of the magnetic casing.

The switch unit 140b is connected to the magnet mounting unit 120b through a switch unit coupling hole 144, and is installed to pass through the opening 136 of the magnetic casing 130b. Accordingly, the switch unit 140b can be operated in the horizontal direction along the opening 136, and the magnet mounting unit 120b can be rotated and moved horizontally with respect to the magnetic force interrupting unit 152 in accordance with the operation of the switch unit 140b.

Specifically, by the operation of the switch unit 140b, the permanent magnets of the same polarity may be placed at the opposite sides of the magnetic force interrupting unit 152, respectively. Alternatively, the permanent magnets 110 of opposite polarities may be placed at the opposite sides of the magnetic force interrupting unit 152, respectively.

Although an elastic member of the second magnetic lock device 100b is not shown, the elastic member may be provided to restore the magnet mounting unit 120b to its original position when the magnet mounting unit is rotated by an external force applied through the switch unit 140b, and then the external force is removed.

Also, although a pyramid fixing unit of the second magnetic lock device is not shown, it may be provided as occasion demands, and the magnetic force amplifying unit 160 may be designed to simultaneously perform the role of the pyramid fixing unit.

Further, the opening 136 of the magnetic casing 130b is formed by partially removing the side surface of the magnetic casing, and may be formed in an elongated hole extending along the side surface of the magnetic casing as occasion demands.

FIGS. 8a and 8b are conceptual views showing a basic principle of attachment and detachment of the artificial limb structure having the magnetic lock device according to the present invention. FIG. 8a shows a detached state and FIG. 8b shows an attached state. Hereinafter, the principle of attachment and detachment of the artificial limb structure having the magnetic lock device according to the present invention will be described with reference to FIGS. 8a and 8b.

Referring to FIG. 8a showing the detached state in which the artificial limb (200 in FIG. 1) and the socket liner unit (300 in FIG. 1) are detached from each other, the permanent magnets of opposite polarities are arranged at the opposite sides of the magnetic force interrupting unit 152, respectively. Accordingly, the magnetic force generated by the permanent magnets 110 acts only inside the magnetic flux control unit 150 without passing therethrough, and the magnetic force does not reach the attachment and detachment member 320. In other words, the artificial limb 200 and the socket liner unit 300 can be separated from each other.

Referring to FIG. 8b showing the attached state in which the artificial limb 200 and the socket liner unit 300 are attached to each other, the permanent magnets of the same polarity are arranged at the opposite sides of the magnetic force interrupting unit 152, respectively. Accordingly, the magnetic force generated by the permanent magnets 110 passes through and acts outside the magnetic flux control unit 150, and the magnetic force reaches the attachment and detachment member 320, so that the permanent magnets 110 and the attachment and detachment member 320 can be attached to each other by the magnetic force. In other words, the artificial limb 200 and the socket liner unit 300 can be coupled to each other.

Hereinafter, the principle of attachment and detachment of the artificial limb structure having the first magnetic lock device 100a and the artificial limb structure having the second magnetic lock device 100b will be described in detail with reference to the basic principle of the present invention described above.

Figure 9A:
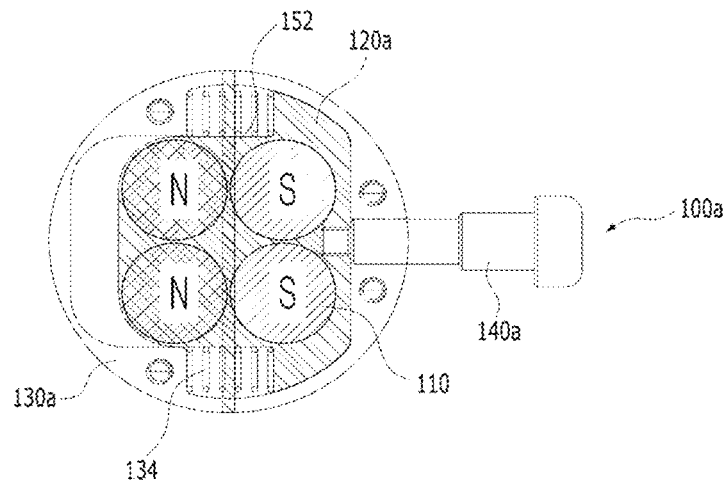
Figure 9B:
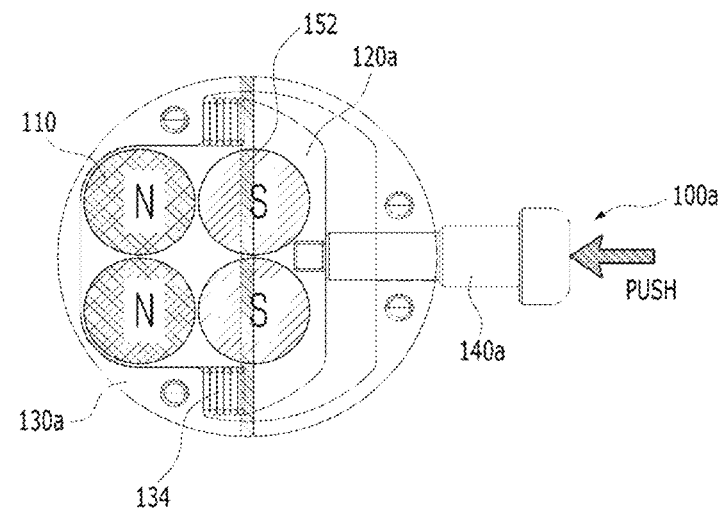

FIGS. 9a and 9b are conceptual views showing the principle of attachment and detachment of the artificial limb structure having the first magnetic lock device 100a. FIG. 9a shows an attached state and FIG. 9b shows a detached state. Hereinafter, the principle of attachment and detachment of the artificial limb structure having the first magnetic lock device 100a will be described with reference to FIGS. 9a and 9b.

Referring to FIG. 9a showing the attached state in which the artificial limb (200 in FIG. 1) and the socket liner unit (300 in FIG. 1) are attached to each other, the permanent magnets of the same polarity are arranged at the opposite sides of the magnetic force interrupting unit 152, respectively. Accordingly, the magnetic force generated by the permanent magnets 110 passes through and acts outside the magnetic flux control unit 150, and the magnetic force reaches the attachment and detachment member 320, so that the permanent magnets 110 and the attachment and detachment member 320 can be attached to each other by the magnetic force. In other words, the artificial limb 200 and the socket liner unit 300 can be coupled to each other.

Referring to FIG. 9b showing the detached state in which the artificial limb (200 in FIG. 1) and the socket liner unit (300 in FIG. 1) are detached from each other, the switch unit 140a is moved in a direction of the magnetic casing 130a (arrow direction) and the magnet mounting unit 120a is then moved linearly, so that the permanents magnets 110 of opposite polarities are arranged at least at one of the opposite sides of the magnetic force interrupting unit 152. Accordingly, the magnetic force generated by the permanent magnets 110 acts only inside the magnetic flux control unit 150 without passing therethrough, and the magnetic force does not reach the attachment and detachment member 320. In other words, the artificial limb 200 and the socket liner unit 300 can be separated from each other.

Figure 10A:
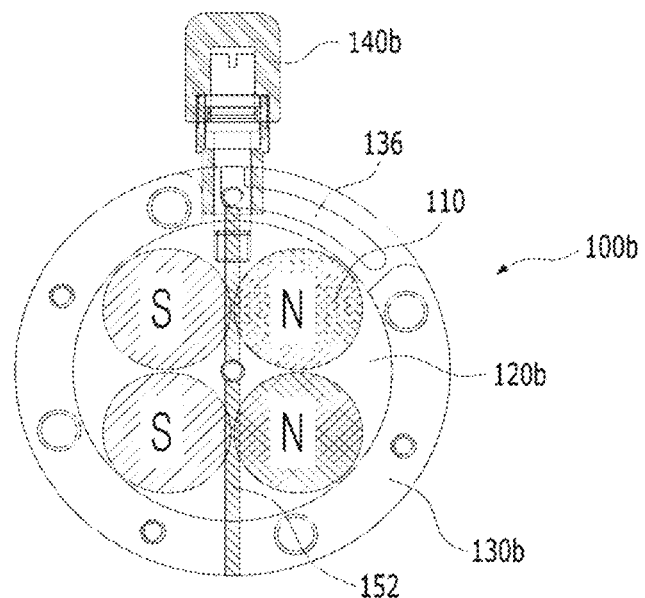
FIGS. 10a and 10b are conceptual views showing a principle of attachment and detachment of the artificial limb structure having the second magnetic lock device 100b.
Figure 10B:
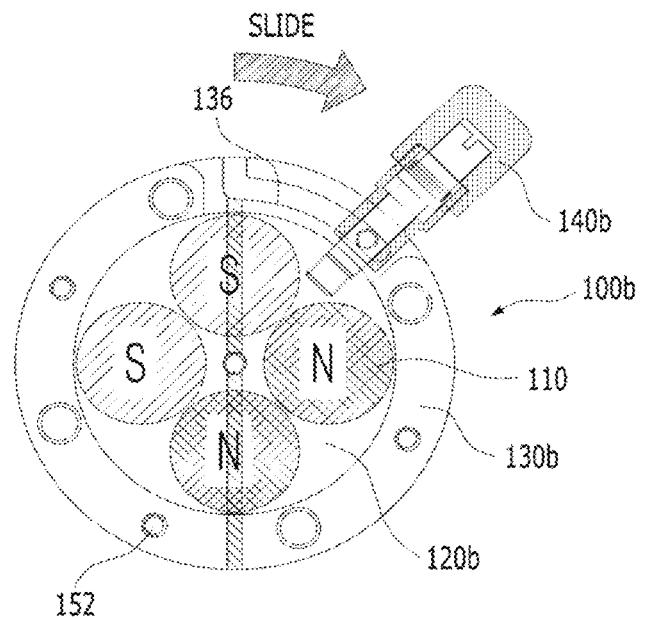

FIGS. 10a and 10b are conceptual views showing the principle of attachment and detachment of the artificial limb structure having the second magnetic lock device 100b. FIG. 10a shows an attached state and FIG. 10b shows a detached state. Hereinafter, the principle of attachment and detachment of the artificial limb structure having the second magnetic lock device 100b will be described with reference to FIGS. 10a and 10b.

Referring to FIG. 10a showing the attached state in which the artificial limb (200 in FIG. 1) and the socket liner unit (300 in FIG. 1) are attached to each other, the permanent magnets of the same polarity are arranged at the opposite sides of the magnetic force interrupting unit 152, respectively. Accordingly, the magnetic force generated by the permanent magnets 110 passes through and acts outside the magnetic flux control unit 150, and the magnetic force reaches the attachment and detachment member 320, so that the permanent magnets 110 and the attachment and detachment member 320 can be attached to each other by the magnetic force. In other words, the artificial limb 200 and the socket liner unit 300 can be coupled to each other.

Referring to FIG. 10b showing the detached state in which the artificial limb (200 in FIG. 1) and the socket liner unit (300 in FIG. 1) are detached from each other, the switch unit 140b is rotated in an arrow direction and the magnet mounting unit 120b is then moved linearly in the direction in which the switch unit is rotated, so that the permanent magnets of opposite polarities are arranged at the opposite sides of the magnetic force interrupting unit 152, respectively. Accordingly, the magnetic force generated by the permanent magnets 110 acts only inside the magnetic flux control unit 150 without passing therethrough, and the magnetic force does not reach the attachment and detachment member 320. In other words, the artificial limb 200 and the socket liner unit 300 can be separated from each other.

A rotation angle of the switch unit 140b in the detached state of FIG. 10b may be greater than 0° and less than 90° from an initial position (attached state of FIG. 10a) based on the magnetic force interrupting unit 152, preferably from 10 to 80°, more preferably from 30 to 60°, and most preferably 45°. In the case of 45°, the permanent magnets 110 arranged at the opposite sides of the magnetic force interrupting unit 152, respectively, can have uniform polarity.

Although the embodiments of the present invention have been described hereinabove, those having ordinary knowledge in the technical field of the present invention will appreciate that various changes and modifications may be made to the embodiments described herein by the addition, modification, removal and the like of elements without departing from the scope and spirit of the present invention as disclosed in the accompanying claims. However, the various changes and modifications are to be construed as being included within the right scope of the present invention. For example, one element presented in the description may be implemented by plural divided elements. Likewise, plural elements presented in the description may be implemented by a unified single element. The scope of the present invention is defined by the accompanying claims rather than the description which is presented above. Moreover, the present invention is intended to cover not only the exemplary embodiments, but also various alternatives, modifications, equivalents and other embodiments that may be included within the spirit and scope of the present invention as defined by the appended claims.

DESCRIPTION OF THE REFERENCE
NUMERALS IN THE DRAWINGS

100: magnetic lock device
100a: first magnetic lock device
100b: second magnetic lock device
110: permanent magnets
120a, 120b: magnet mounting unit
130a, 130b: magnetic casing
132: magnet receiving hole
134: elastic member
136: opening
140a, 140b: switch unit
142a: switch unit coupling hole a
142b: switch unit coupling hole b
144: switch unit coupling hole
150: magnetic flux control unit
152: magnetic force interrupting unit
160: magnetic force amplifying unit
170: pyramid fixing unit 200: artificial limb
210: artificial limb body
220: artificial limb connecting pyramid
230: artificial limb connecting adaptor
300: socket liner unit
310: socket liner umbrella
320: attachment and detachment member
330: socket liner

The invention claimed is:

1. An artificial limb structure having a magnetic lock, the artificial limb structure comprising:
   an artificial limb coupled at an upper end thereof to the magnetic lock; and
   a socket liner detachably coupled to the magnetic lock coupled to the artificial limb,
   wherein the socket liner includes an attachment and detachment member attachable and detachable to or from the magnetic lock by a magnetic force, and
   the magnetic lock includes:
   permanent magnets;
   a magnetic flux controller provided on the permanent magnets and transmitting the magnetic force generated by the permanent magnets to the attachment and detachment member or interrupting a transmission of the magnetic force;
   a magnetic force interrupter provided at the magnetic flux controller and interrupting magnetic forces between permanent magnets arranged at opposite sides of the magnetic force interrupter;
   and a switch adjusting an arrangement of the permanent magnets with respect to the magnetic force interrupter;
   (1) when the permanent magnets of the same polarity are placed at the same side and the permanent magnets are placed at the different sides with respect to the magnetic force interrupter, respectively, the magnetic lock and the attachment and detachment member are attached to each other, or
   (2) when the permanent magnets of opposite polarities are placed together at the first side and/or the second side with respect the magnetic force interrupter the magnetic lock and the attachment and detachment member are detached from each other.

2. The artificial limb structure of claim 1, wherein the switch allows the permanent magnets to be moved linearly and horizontally so that a relative arrangement of polarities of the permanent magnets to the magnetic force interrupter is changed.

3. The artificial limb structure of claim 1, wherein the switch allows the permanent magnets to be rotated and moved horizontally so that a relative arrangement of polarities of the permanent magnets to the magnetic force interrupter is changed.

4. The artificial limb structure of claim 1, wherein the magnetic lock further includes:
   a magnet mount in which the permanent magnets are installed; and
   a magnetic casing provided with a magnet receiving hole receiving therein the magnet mount,
   wherein the magnetic flux controller is provided on the magnetic casing and transmits the magnetic force generated by the permanent magnets to the attachment and detachment member or interrupts the transmission of the magnetic force,
   the magnetic force interrupter is linearly provided at a center of the magnetic flux controller and interrupts the magnetic forces between the permanent magnets arranged at the opposite sides of the magnetic force interrupter, and
   the switch is connected to the magnet mount and adjusts the arrangement of the permanent magnets with respect to the magnetic force interrupter.

5. The artificial limb structure of claim 4, wherein the switch is connected to the magnet mount, and is installed to pass through a side surface of the magnetic casing, the switch allowing the permanent magnets to be moved linearly in a direction perpendicular to the linear magnetic force interrupter so that a relative arrangement of polarities of the permanent magnets to the magnetic force interrupter is changed.

6. The artificial limb structure of claim 4, wherein the magnetic casing is provided with an opening partially formed at a side surface of the magnetic casing, and the switch is connected to the magnet mount and is installed to pass through the opening of the magnetic casing, the switch allowing the permanent magnets to be rotated and moved linearly with respect to the linear magnetic force interrupter so that a relative arrangement of polarities of the permanent magnets to the linear magnetic force interrupter is changed.

7. The artificial limb structure of claim 4, further comprising:
   a magnetic force amplifier provided at a lower portion of the magnetic casing and amplifying the magnetic force generated by the permanent magnets.

8. The artificial limb structure of claim 4, wherein the artificial limb structure having the magnetic lock further includes:
   a socket receiving therein the socket liner and connected to an outer circumferential surface of the magnetic lock.

9. The artificial limb structure of claim 4, further comprising:
   an elastic member connecting the magnet mount and the magnetic casing to each other, and restoring the magnet mount to its original position when an external force to move the magnet mount is removed.

10. The artificial limb structure of claim 4, wherein the socket liner includes:
    a socket liner umbrella;
    a socket liner part provided at an upper end of the socket liner umbrella and applied to a stump of a wearer; and
    the attachment and detachment member attached to a lower portion of the socket liner umbrella, and attachable and detachable to or from the magnetic lock by the magnetic force, the attachment and detachment member being made of a metal material.

11. The artificial limb structure of claim 10, wherein the socket liner part includes a silicone material.

12. The artificial limb structure of claim 11, wherein an inner surface of the socket liner part that is in contact with the stump of the wearer is made of a silicone material having a Shore A hardness ranging from 3 to 20.

13. The artificial limb structure of claim 11, wherein an outer surface of the socket liner part that is in contact with the socket liner umbrella is attached with a SPANDEX fabric, or the outer surface of the socket liner is covered with a chemical vapor deposited poly(p- xylylene) coating.

* * * * *